• United States Patent 
Harrison et al.

(10) Patent No.: US 6,775,000 B2
(45) Date of Patent: Aug. 10, 2004

(54) METHOD AND APPARATUS FOR WAFER-LEVEL TESTING OF SEMICONDUCTOR LASER

(75) Inventors: James Harrison, Morgan Hill, CA (US); David Leslie Heald, Solvang, CA (US)

(73) Assignee: Novalux, Inc., Sunnyvale, CA (US)

( * ) Notice: Subject to any disclaimer, the term of this patent is extended or adjusted under 35 U.S.C. 154(b) by 397 days.

(21) Appl. No.: 10/033,975

(22) Filed: Dec. 19, 2001

(65) Prior Publication Data

US 2003/0164707 A1 Sep. 4, 2003

(51) Int. Cl.[7] .............................................. G01N 21/00
(52) U.S. Cl. ..................... 356/432; 356/237.5; 324/767
(58) Field of Search .............................. 356/432–440, 356/237.1–237.5; 324/767, 760, 765; 372/43, 45, 50, 46

(56) References Cited

U.S. PATENT DOCUMENTS

| | | | | |
|---|---|---|---|---|
| 5,260,772 A | * | 11/1993 | Pollak et al. | 356/417 |
| 5,422,498 A | * | 6/1995 | Nikawa et al. | 257/48 |
| 5,498,973 A | | 3/1996 | Cavaliere et al. | 324/765 |
| 6,057,918 A | | 5/2000 | Geary et al. | 356/218 |
| 6,137,305 A | | 10/2000 | Freund et al. | 324/767 |
| 6,255,707 B1 | | 7/2001 | Bylsma et al. | 257/414 |
| 6,264,852 B1 | | 7/2001 | Herchen et al. | 216/60 |
| 6,448,805 B1 | * | 9/2002 | Heald et al. | 324/767 |

* cited by examiner

*Primary Examiner*—Hoa Q. Pham
(74) *Attorney, Agent, or Firm*—Fay Kaplun & Marcin, LLP

(57) ABSTRACT

A system and method for manufacturing and wafer-level testing properties of a wafer comprises a chuck receiving a wafer to be tested and a pump light source directing an output beam toward selected locations on a wafer received on the chuck in combination with a laser light detector detecting light emitted from the wafer and a pump beam aiming mechanism selectively varying a position at which the pump light source output beam enters the wafer.

31 Claims, 3 Drawing Sheets

METHOD AND APPARATUS FOR WAFER-LEVEL TESTING OF SEMICONDUCTOR LASER

FIELD OF THE INVENTION

The present invention relates to a method and apparatus for testing semiconductor lasers, and more specifically relates to a method and apparatus for wafer-level testing of vertical cavity surface emitting lasers prior to their complete assembly.

BACKGROUND OF THE INVENTION

Semiconductor lasers in use today can generally be classified as edge-emitting diode lasers and vertical cavity surface emitting lasers ("VCSELs"). In an edge-emitting laser, a semiconductor gain medium, for example a quantum-well semiconductor structure, is formed as a region deposited on a semiconductor substrate, or wafer. Many devices are typically formed from one single wafer, and once an individual device has been detached from the wafer, mirrors are formed or otherwise positioned on opposite edges of the gain medium, perpendicular to the substrate surfaces. The assembly forms a resonant cavity within which the gain medium is located. Electrical or optical pumping of the gain medium generates a laser beam which propagates in a direction along the plane of the substrate. Edge-emitting lasers thus generate a beam in a direction along the plane of a substrate forming the laser, exiting the device at an edge where the devices are separated into individual units. It is thus not practical to test these devices prior to separating them into individual units, thereby exposing the edges from which the beams are output.

VCSEL's, in contrast, generate output beams in a direction perpendicular to the plane of a substrate on which they are formed. Thus the orientation of individual VCSELs on a wafer substrate, prior to being separated from one another, is potentially suitable for testing before carrying out the manufacturing steps that lead to separation. Conventional testing methods used on VCSELs involve electrically probing the optical aperture side of a wafer, and detecting light emitted from that side while shorting the opposite side of the wafer to ground. Conventional testing methods and devices do not provide a way to screen and map optical characteristics of epitaxial wafers prior to processing the wafer beyond epitaxial growth.

SUMMARY OF THE INVENTION

The present invention is directed to an apparatus for testing properties of a wafer having disposed thereon layers that form all or part of a lasing cavity, the apparatus comprising a chuck receiving a wafer to be tested and a pump light source directing an output beam toward selected locations on a wafer received on the chuck in combination with a laser light detector detecting light emitted from the wafer and a pump light source aiming mechanism selectively varying a position at which the pump light output beam enters the wafer.

In another aspect, the invention is directed to a method of wafer-level testing of semiconductor laser devices, comprising the steps of positioning a wafer to be tested in a predetermined position relative to a pump light source, optically pumping preselected regions of the wafer with the pump light source, and analyzing light emitted from each of the preselected regions to determine the laser-related characteristics of the preselected regions of the wafer.

DETAILED DESCRIPTION

The present invention is a method and apparatus for testing semiconductor lasers at the wafer-level. The invention allows testing a wafer's laser characteristics before the wafer has been separated into the individual laser devices, and before additional processing steps are carried out to add electrodes and insulators to the laser devices. During manufacturing of the laser devices, a plurality of devices are formed from a single wafer. For example, 4000 individual devices may be formed on a 4 in. diameter wafer. In the context of this application, the term wafer is used to refer to the assembly of several layers that may include a substrate, reflective structures and an active gain region. The active region is a region in a laser device where light is generated, and may contain quantum wells, quantum dots, or other light-generating structures, and may include other structures (for example barrier layers, which absorb energy and transfer it to the light-generating structures).

According to the present invention, although the completed devices may be electrically pumped lasers, the active regions of the devices are pumped optically in order to test their optical characteristics, for example laser characteristics such as wavelength, power output, efficiency, etc. or laser-related characteristics such as gain. That is, the active regions of the devices may be excited by either electric or optical energy, but optical pumping may be accomplished at an earlier manufacturing stage than electrical pumping, since electrical pumping requires electrodes and insulators that are typically added to the wafer in later stages of manufacturing.

A typical VCSEL manufacturing process begins with the growth of epitaxial layers on a wafer substrate, including for example a p-side mirror, an active region that may contain quantum wells, and a n-side mirror. At this point, the epitaxial layers are relatively uniform, except for non-uniformities caused by the epitaxial growth process itself. Thereafter, the wafer may be further processed to add electrodes, insulators and various metal components to each device, and other structures that individualize or otherwise define the devices are also included. After epitaxial growth, the wafer may be cleaved along device boundaries to separate the devices from one another, and any required final assemblage is performed to complete the individual devices or, for example lines or arrays of devices. The testing according to the present invention may take place at any time after the growth of the epitaxial layers.

Figure 1:
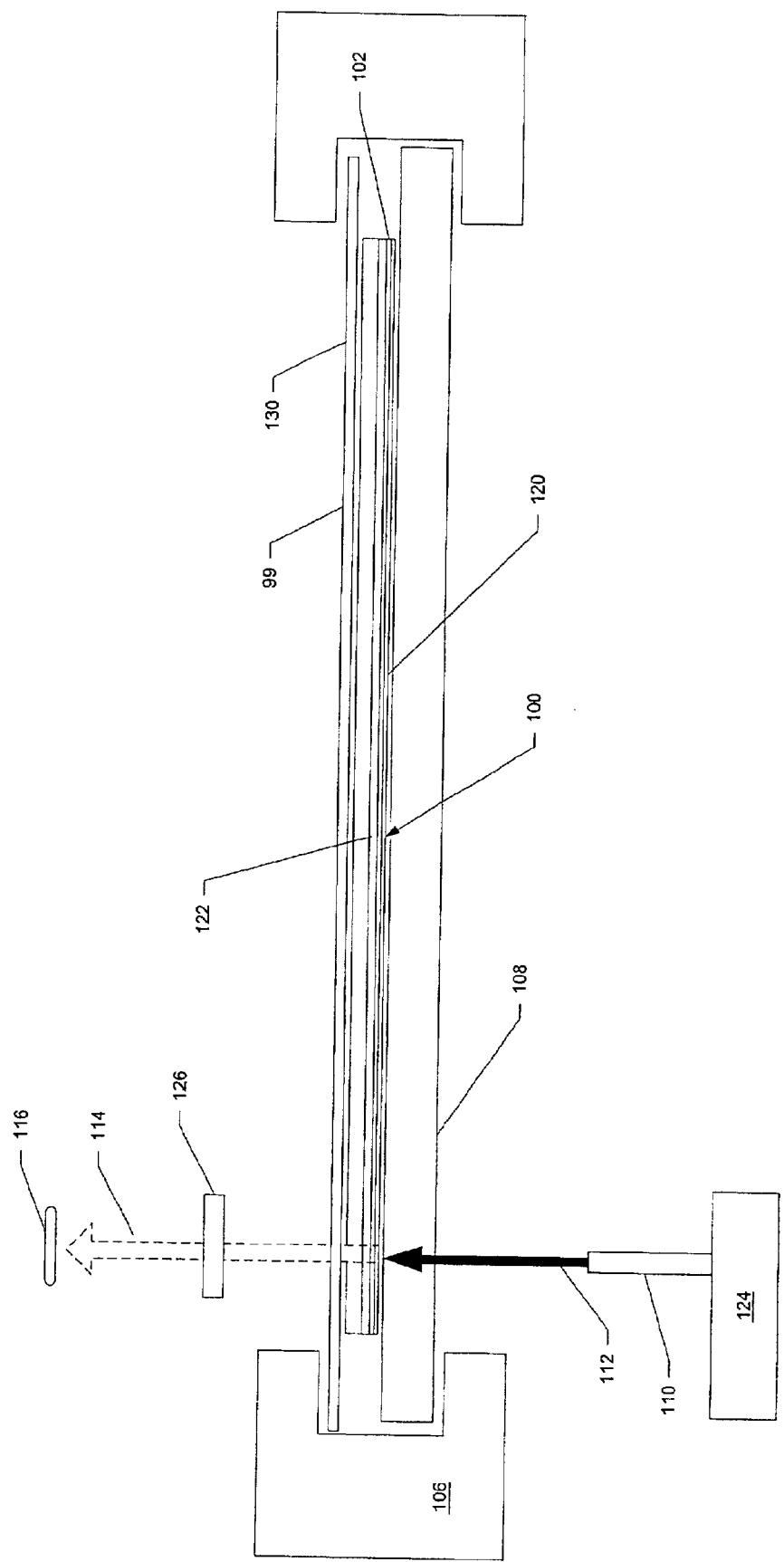
FIG. 1 is a side view showing an embodiment of the wafer-level testing apparatus for semiconductor lasers according to the invention.

FIG. 1 shows a cross section of an embodiment of a VCSEL testing apparatus according to the present invention. A semiconductor wafer 100 is positioned in the device for testing after the epitaxial layers of the wafer have been grown. Those of skill in the art will understand that the testing of the wafer 100 may be performed at any time after the epitaxial layers have been formed. However, it is preferable to perform this testing before any additional steps in the VCSEL manufacturing process have been performed as unsuitable wafers, or unsuitable wafer portions, or important laser characteristics (e.g., laser wavelength) may be identified before additional expenditures of time and effort are made. The wafer 100 described as being tested in regard to the apparatus according to this embodiment of the invention includes an active region 102 epitaxially grown on a substrate 99, and two mirror regions 120, 122 that are also grown epitaxially. The testing apparatus includes a chuck 108 on which the wafer 100 is positioned and retained in place mechanically by, for example, clamps, a flange or vacuum pressure. As shown in FIG. 1, a pair of C-clamps 106 may be used to retain chuck 108 in place at the desired location.

Chuck 108 may be made, for example, of fused silica, sapphire, or any other material that is transparent to the wavelength of a pump light source 110 to be employed in the system, and to the wavelength of an output beam of wafer 100. Alternatively, the chuck 108 may be opaque to either or both of these wavelengths of light. In this case, openings may be provided to form windows over portions of wafer 100 corresponding to input and output areas of each of the individual laser devices or arrays of devices that will be tested, as described in more detail below. Since the pump light may enter the active region from either the top or the bottom, it may not be necessary to provide a chuck 108 that is transparent to the wavelength of the pump light.

The test apparatus includes a pump light source 110 that generates a beam 112 having a wavelength appropriate to pump energy into the active region 102, to induce the output of laser light. The pump light source may be, for example, a laser such as a semiconductor, gas, or solid state laser device, or another appropriate light source such as a lamp or light emitting diode ("LED"). Those skilled in the art will understand that an appropriate pumping wavelength depends on the characteristics of the materials and structures included in the wafer 100. Preferably, the wavelength of the pump light source 110 should be largely absorbed by active region 102, but other epitaxial layers of the device, such as those forming mirrors 120, 122 should be relatively transparent to beam 112. In one embodiment, mirrors 120, 122 may be highly reflective to the wavelength of light generated by the laser device, thus the pump light beam 112 should have a wavelength different from the output laser wavelength, to avoid being reflected by the mirrors 120, 122. In another embodiment, the pump light wavelength may be closer to the laser wavelength because, for example, a mirror through which it is transmitted is less reflective, the pump light is sufficiently bright to penetrate a mirror, or the structures of the laser device are arranged such that the pump light does not have to travel through a mirror. In this exemplary embodiment, the laser beam from the tested wafer may be discriminated from any reflected pump light using an optical band pass filter or other dispersive optics.

In the exemplary case of an output beam 114 having a wavelength of 980 nm, mirrors 120, 122 may preferably be especially reflective within a stop band about 100 nm wide, centered near 980 nm. In this case, the pump light beam 112 should have a wavelength of less than about 930 nm to avoid the mirror stop band. As the pumping light must also have greater energy than the output laser light in order to excite the active region, the wavelength of the pump light must be shorter than that of the output light, as energy per photon increases as the wavelength of light decreases. Thus, although pumping light of more than about 1030 nm would also avoid the stop band of mirrors 120, 122, such light would likely not have enough energy to pump the active region 102.

Pump beam 112 may have, in one embodiment, a power level of about $1 \times 10^5$ W/cm$^2$, in a beam diameter of 100 microns. In one embodiment, the pump light source 110 is operated in a pulse mode, with short bursts of light generated. Thus, a pump light source with a low duty factor may be preferred for this application. The "duty factor" of a light source operated in pulsed mode is the ratio of the time "on" to the sum of the time "on" plus the time "off". For example, a laser operated with 10 microsecond pulses, spaced 90 microseconds apart, will have a duty factor of 0.1 or 10 percent. Operating in the pulse mode makes possible the production of high intensity of pump light, while maintaining an average power provided to the wafer 100 over time low enough to avoid excessive heating of the wafer 100. For example, in one embodiment of the invention a duty factor of 10 percent might be used to achieve an average power level of 1 W using a pump light source with a peak power output of 10 W. The pulse widths used in this case might be in the range of 0.1 to 100 microseconds, with corresponding "off" periods calculated accordingly. Any number of pump light sources could be used in this embodiment of the invention, for example, a solid state Ti doped sapphire laser or a GaAs edge emitter laser may be employed as the pump light source 110 of this embodiment.

The testing apparatus shown in FIG. 1 also includes an aiming mechanism with a drive 124 for the laser 110. Drive 124 is designed to accurately move pump light source 110 along wafer 100 to locations on wafer 100 where individual semiconductor laser devices will be formed. In this manner it is possible to characterize the laser properties of the epitaxially grown layers at all the locations that may become devices. The movement of pump light source 110 may be optimized for the geometry of wafer 100. For example, if the devices will be formed on wafer 100 in a rectangular array of regularly spaced rows and columns, drive 124 moves the laser 110 relative to the wafer 100 to direct an output beam 112 from the laser 110 sequentially through all the rows and columns of the wafer 100. Each of the selected locations on the wafer 100 corresponds to a selected one of the devices, so that the beam 112 stimulates emission from the selected device so that the properties of the epitaxial layers at that location may be determined. The pump beam 110 is then directed to the next desired location to test the properties of the epitaxial layers at that next location. A measuring system may also be included in drive 124, to accurately control the positioning of beam 112 on the wafer 100.

In a different embodiment, the pump light source 110 may be stationary, and the chuck 108 with wafer 100 can move relative to pump beam 112. As long as the position of pump beam 112 is known relative to wafer 100, it does not matter which component moves and which is stationary. In this embodiment, the wafer may be accurately positioned and stepped in relation to the pump light beam by an aiming mechanism including a probing station machine such as a Signatone XXC Probe Station with an S-LDC2 Dry/Dark Chamber or CM512 Probe Station available from Signatone Corporation, Gilroy, Calif. or a Suss PA 200 Semiautomatic Probe System available from SUSS MicroTec, Garching, Germany. In another embodiment, pump light source 110 and the assembly of chuck 108 and wafer 100 are both stationary. The pump beam 112 is aimed at the appropriate position over wafer 100 by a system of adjustable focusing mirrors, lenses, and/or other optics.

In yet another embodiment, an array of pump beams may be used to simultaneously probe several locations on the wafer. The beams may be generated by an array of pump light sources, or by a single pump light source in conjunction with beam splitting optics. A corresponding array of detectors for the emitted beams may also be provided to simultaneously analyze the emitted beams emitted from the various devices to determine the properties of the epitaxial layers at each location.

Although determining the properties of the spatial mode of the emission of the wafer 100 has been discussed above, other modes may be examined as well. For example, different spot sizes of the pump beam 112 may be used to stimulate emissions from wafer 100 in different modes. A beam 112 of small size may be used to characterize the spatial mode, while larger size beams may be used to stimulate emission of higher order modes. Particularly, this application might be used in an embodiment employing a curved mirror or lens as part of the laser cavity of the laser being tested. For example, curved lenses may be etched into the wafer substrate or employed as an external mirror to create an external cavity for the laser device.

The exemplary testing apparatus shown in FIG. 1 also includes a detector 116 positioned on the opposite side of wafer 100 from the pump light source 110. In this example, detector 116 is aligned collinearly with pump light source 110 to receive the emitted laser beam 114, and to analyze its properties. For example, the energy of emitted beam 114 may be measured and related to the energy of pump beam 112. The wavelength and the modes of the beam 114 may also be measured to build a two dimensional map of the laser properties of the wafer 100. Other qualities of the emitted laser beam 114 may also be measured by detector 116, such as the phase uniformity and spectral coherence of the emitted light. Detector 116 may also be linked to drive 124 or to a separate drive, so that the detector 116 is always aligned with a laser currently being stimulated by the pump light source 110 to receive the beam 114 emitted therefrom.

In the embodiment shown in FIG. 1, the wafer 100 is oriented on chuck 108 so that totally reflective mirror 120 (a p-doped mirror in this case) faces chuck 108, while partially reflective mirror 122 (an n-doped mirror in this embodiment) faces detector 116. Emitted beam 114 thus exits the device as shown in the drawing, towards detector 116. Most if not all of the pump beam 112 is absorbed by the active region 102 of wafer 100. However, an optical filter 126 may be placed in the path of emitted beam 114 to remove any portion of pump beam 112 that may otherwise affect the characterization of emitted beam 114.

A third mirror 130 may be included in the testing apparatus according to the invention. Mirror 130 is part of the testing apparatus, and is not included in the final laser device. However, during testing of the wafer 100, third mirror 130 is placed in close proximity of the wafer 100 surface, so that it becomes a part of an extended resonant cavity that produces the emitted laser beam 114. In the exemplary embodiment shown in FIG. 1, third mirror 130 is placed adjacent the partially reflective mirror 122 side of the wafer, so that it reflects a portion of emitted beam 114 back into the resonance cavity.

The third mirror 130 may be used in the testing apparatus to lower the laser threshold of the epitaxial layers being tested, significantly reducing the intensity of the pump beam 114 required to induce the test specimen to lase. The separation from wafer 100 and the curvature of third mirror 130 also help define the modes of laser light emitted by the specimen. In particular, third mirror 130 may be designed to help define the spatial mode of the emitted laser, which results in lasing with a lower intensity pump light. The mode of the emitted laser beam 114 is also affected by the size of the probe's pump beam, however an appropriate third mirror 130 can have a major effect in defining the spatial mode. In a preferred embodiment, third mirror 130 is a curved mirror, however flat mirrors may also be used, but may result in additional higher order modes existing in the emitted beam 114, requiring more intense optical pumping. In an alternative embodiment, a mirror such as the one shown in FIG. 1 as mirror 130 may be used in connection with a wafer having only a single mirror and an active gain region. In this case, the device will only lase in the presence of a mirror that is separate from the wafer.

Figure 2:
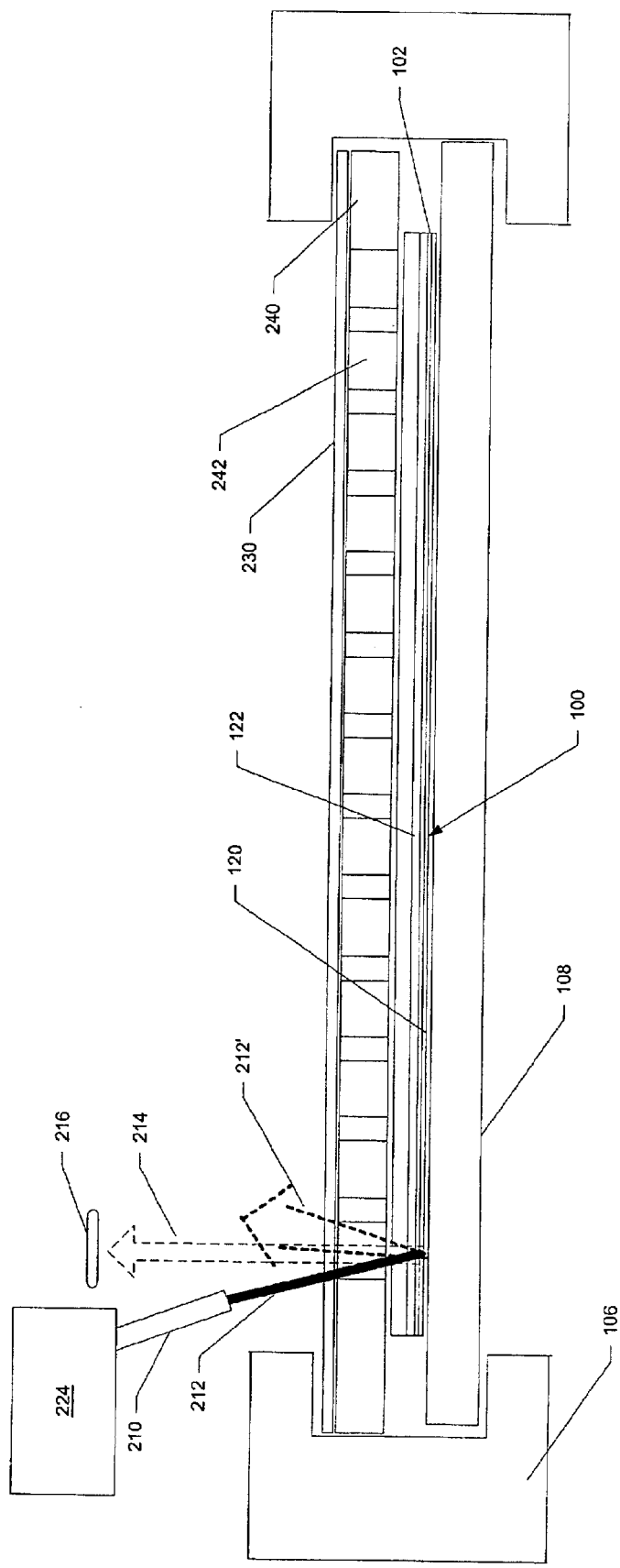
FIG. 2 is a side view showing a second embodiment of the wafer-level testing apparatus for semiconductor lasers according to the invention.

FIG. 2 shows a second embodiment of the wafer-level test apparatus according to the invention. In this example, the pump light source 210 and the detector 216 are located on the same side of wafer 100. In the example, pump light source 210 generates a pump beam 212 that is directed to a specified location on wafer 100 by an aiming mechanism 224. If the wavelength of pump beam 212 is selected to be partially reflected by mirror 120, a reflected beam 212' may exit the wafer 100. In this configuration pump beam 212 only travels through partially reflective mirror 122 before reaching the active region 102, and any light not absorbed by the active region is reflected by mirror 120. This configuration may be advantageous because it permits tailoring the wavelengths of the pump light source over a greater range, without having to avoid the stop band of the totally reflective mirror 120.

The embodiment shown in FIG. 2 also includes a wafer clamp. Wafer clamp 240 helps to hold wafer 100 in place while it is being moved relative to pump light source 210, and also helps to flatten wafer 100 in cases where the epitaxial growth steps result in significant the wafer bowing. Wafer clamp 240 may also be used as a spacer to control the size of the resonant cavity formed by the epitaxial layers and the third mirror 230. This arrangement may be used to simulate a category of VCSEL devices known as Vertical Extended Cavity Surface Emitting Laser (VECSEL), which include optional spacers disposed between the active region and one or both of the top and bottom mirrors. These spacers are used to achieve desired dimensions of the lasing resonant cavity between the mirrors.

Figure 3:
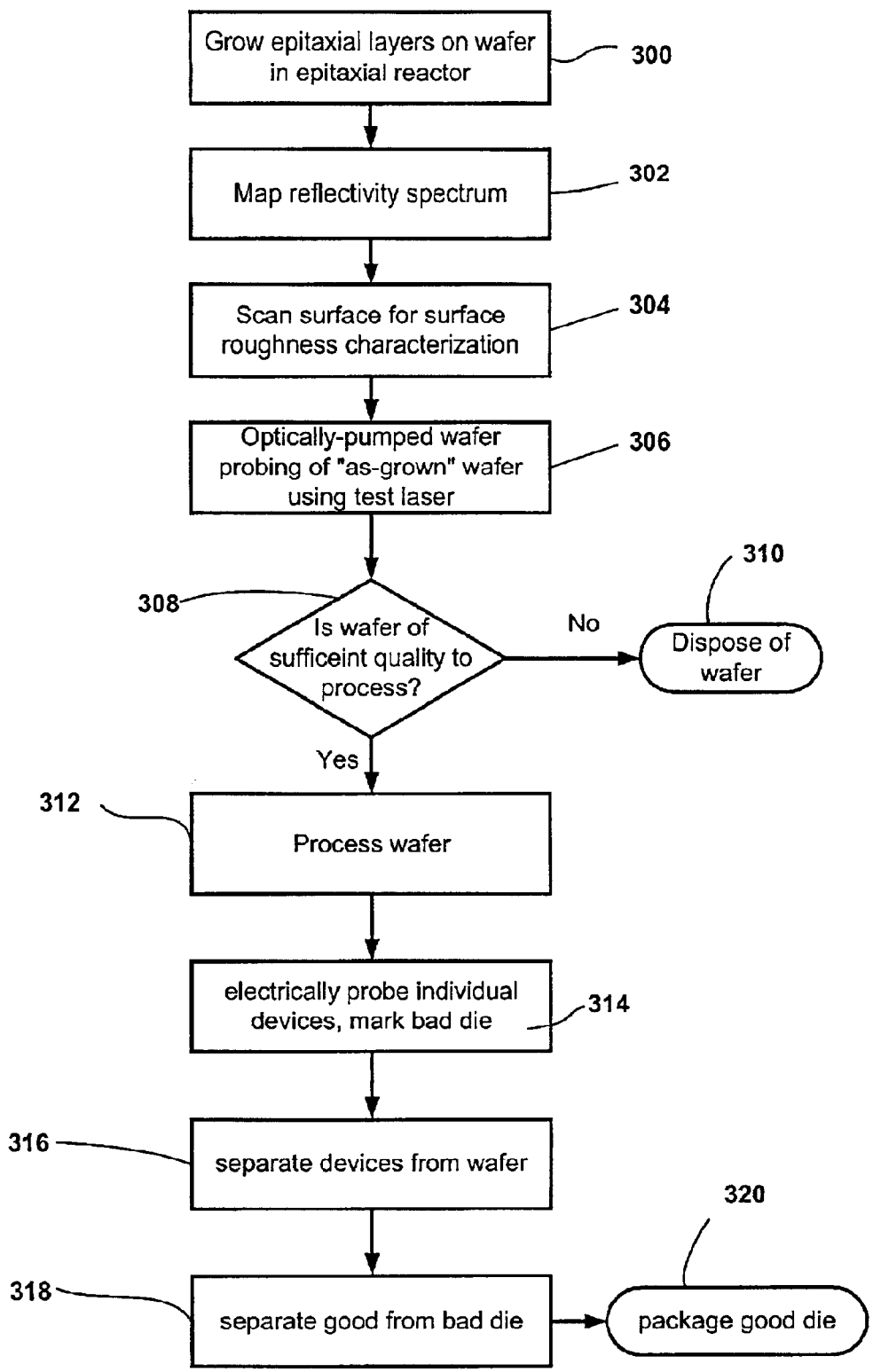
FIG. 3 is a flow chart showing exemplary manufacturing steps for forming semiconductor lasers devices on a wafer, including testing according to an embodiment of the invention.

FIG. 3 is a flow chart showing an exemplary method for manufacturing semiconductor laser devices, which includes carrying out the wafer-level testing according to one embodiment of the invention. The process starts with growing epitaxial layers on a substrate of a wafer in step 300. The epitaxial layers that are grown in an epitaxial reactor may include an active gain region comprised of, for example, layers of InGaAs and GaAsP, and mirror regions made for example of AlGaAs, with alternating layers having different concentrations of Al and Ga to create layers with different refractive indices. The epitaxial layers may be grown using conventional methods, such as metallo-organic chemical vapor deposition (MOCVD) or molecular beam epitaxy (MBE). As explained above, the epitaxial growth may be carried out in one step, or in several steps during a regrowth process. In the latter case, some or all of the testing and characterization steps may be performed between growth phases of the layers.

Steps 302 and 304 describe optional tests that may be carried out to initially evaluate the suitability of the epitaxial layers. In step 302 the reflectivity spectrum is mapped by shining a white light on the surface of the layers, and measuring the reflection at known locations as a function of wavelength. The surface of the wafer is scanned in step 304 to characterize its roughness. Steps 302 and 304 are useful to verify the uniformity and the mechanical properties of the epitaxial layers, before proceeding with more complex and expensive testing and manufacturing steps (e.g., dielectric deposition, ion implant, metal deposition and related lithography, and etch steps required to define specific device features.

Step 306 encompasses the optical pumping of selected areas of the wafer to characterize its lasing properties. As described above, the wafer may be probed to map how the optical characteristics of the epitaxial layers vary, and to determine the characteristics of the individual devices that will be made from the wafer. The mapping is also useful to adjust the various successive processing steps to maximize the number of usable devices that can be obtained from the wafer. The characterization step 306 thus provides information on the overall quality of the wafer being tested, as well as a mapping of those qualities across the wafer.

With the information from step 306 available, a decision may be made in step 308 whether the wafer is of sufficient quality to continue processing, or whether to dispose of the wafer in step 310. Disposing of the wafer may be warranted if more than a given percentage of the wafer does not meet minimum requirements for useful devices. For example, if the optical pumping test shows that more than 20% of the wafer does not emit laser light having an intensity, wavelength and mode within specified tolerances, the wafer may be discarded. For example, for one application, the emitted wavelength may be required to be in the range of 975 nm, plus or minus 3 nm.

Step 306 includes building a map of the wafer's emission properties, which can be used in one embodiment to modify the successive process steps that add structures to individualize the laser devices. For example, the various electrodes, spacers, insulators and other elements that define the individual laser devices may be added to portions of the wafer that have acceptable characteristics, while portions of the wafer having unacceptable properties may be left as they are, to be discarded after the individual devices are cut from the wafer.

In step 312, post-epitaxial growth processing is performed on the wafer. This processing may include the processes that define the individual laser devices, as well as other manufacturing processes that help create the laser device. These known semiconductor processing techniques may include ion implantation for current confinement, insulator deposition (for example SiN), lapping to reduce the thickness of the wafer, and polishing. Some process steps are specific to devices that will be electrically pumped, such as forming electrical contacts by p-metal and n-metal deposition, while other steps can apply to all devices, such as the photoresist and etching steps used to form mesa structures, apertures, contact shapes, and other features of the device. These steps may vary depending on the specific device being manufactured.

Step 314 includes an additional test of the laser characteristics of the processed device. This test may be carried out with an electronic probe, where each of the individual semiconductor laser devices is electrically pumped by the probe, while still a part of the wafer. Detectors are used to evaluate the output laser beam, and devices that do not produce a beam within specifications are marked as bad. An optical pump probe as used in step 306 may also be used for this evaluation step, especially in the case of laser devices that are to operate as optically pumped devices.

The individual laser devices are separated in step 316. The wafer is scribed along the boundaries of the devices, and is cut to individualize the devices. The good and bad devices, as determined in steps 306 and 314, are separated in step 318. The bad devices are discarded, and the good devices are packaged and assembled for completion.

In another embodiment of the present invention, rather than simply separating good wafers from bad wafers or good die from bad die, the wafers or die may be sorted according to the information determined in the probe steps. For example, wafers may be separated into categories according to wavelength, efficiency, or other laser-related characteristics. This may be done, for example, to separate wafers into different inventory groups according to quality or other characteristics. In addition, wafers having certain characteristics may be processed toward specific applications. For example, one application may require a laser producing exactly 980 nm wavelength light, while another application may have a tolerance for light anywhere between, for example, 974 nm-986 nm. Depending on the optical characteristics determined in step 306, a wafer may receive different post-epitaxial growth processing. For example, a higher quality wafer might receive more expensive processing for use in a higher-end product while a usable, but lower quality wafer might receive cheaper processing for use in a less expensive product. Similarly, the data collected by probing a wafer may be used to separate the highest quality die from lower quality die.

The embodiments of the invention described herein are illustrative only, and those skilled in the art will understand that many variations and modifications of the invention may be made, without departing from the scope of the invention. The invention is thus intended to be only limited by the scope of the claims appended thereto.

What is claimed is:

1. An apparatus for testing properties of a semiconductor laser wafer, the apparatus comprising:
   a chuck receiving a wafer to be tested;
   a pump light source directing a pump light beam toward selected locations on the wafer;
   a light detector detecting light emitted from the wafer; and
   a pump beam aiming mechanism selectively varying a position at which the pump light beam enters the wafer.

2. The apparatus according to claim 1, further comprising a light detector positioning mechanism moving the light detector to a position corresponding to a current position at which the pump light beam enters the wafer.

3. The apparatus according to claim 1, further comprising a mirror disposed parallel to a wafer receiving surface of the chuck.

4. The apparatus according to claim 3, wherein the mirror is external to a lasing cavity of the wafer and is shaped to define a mode supported by the lasing cavity of a wafer currently being tested.

5. The apparatus according to claim 1, further comprising a measuring system determining a position of the pump light source relative to the wafer.

6. The apparatus according to claim 5, wherein the pump light beam of the pump light source impinges on a wafer received on the chuck at a selected angle.

7. The apparatus according to claim 1, wherein both the pump light source and the light detector face a first side of the wafer.

8. The apparatus according to claim 1, wherein the pump light source faces a first surface of the wafer, and the light detector faces a second surface of the wafer.

9. The apparatus according to claim 1, wherein the chuck is substantially transparent to the pump light beam.

10. The apparatus according to claim 1, further comprising a wafer clamp adapted for retaining a wafer to be tested in a predetermined position on the chuck.

11. A method of wafer-level testing semiconductor laser devices, comprising the steps of:

positioning a wafer to be tested in a predetermined position relative to a pump light source;

optically pumping preselected regions of the wafer with the pump light source; and analyzing laser light emitted from each of the preselected regions to determine lasing characteristics of the preselected regions.

12. The method according to claim 11, further comprising the step of generating a two dimensional map of lasing characteristics of the wafer based on the analysis of the emitted laser light.

13. The method according to claim 11, further comprising the step of mapping a reflectivity spectrum of epitaxial layers of the wafer.

14. The method according to claim 11, further comprising scanning the epitaxial layers of the wafer to characterize surface roughness.

15. A method of manufacturing semiconductor laser devices on a wafer, comprising:

growing epitaxial layers on the wafer, the epitaxial layers forming at least one mirror and an active gain region;

optically pumping selected regions of the active gain region with a pump light source;

analyzing laser light emitted from each of the regions in response to the optical pumping; and identifying the regions having acceptable characteristics based on the analysis of the emitted light.

16. The method according to claim 15, where the regions corresponding to the semiconductor laser devices are sequentially optically pumped along successive rows and columns of the regions.

17. The method according to claim 15, further comprising the steps of:

performing post epitaxial growth processing on the wafer;

separating the wafer into individual semiconductor laser devices;

sorting the individual semiconductor laser devices based on the analysis of the emitted light.

18. The method according to claim 17, wherein the step of performing post epitaxial growth processing on the wafer includes forming an electrical contact on the wafer.

19. The method according to claim 18, further comprising the step of electrically probing individual laser devices via the electrical contacts.

20. The method according to claim 15, further comprising the step of discarding the wafer when a percentage of regions having acceptable characteristics does not exceed a selected percentage.

21. The method according to claim 15, further comprising the step of disposing an external mirror in proximity to the wafer before optically pumping, the external mirror defining modes of the emitted laser light.

22. A method of manufacturing semiconductor laser devices, comprising:

growing epitaxial layers on a substrate defining at least a mirror region and an active gain region;

optically pumping selected portions of the active gain region with a pump light source;

analyzing light emitted from each of the selected portions in response to the optical pumping to determine laser-related characteristics of the epitaxial layers; and performing post-epitaxial growth processing on at least one of the substrate and the epitaxial layers.

23. The method according to claim 22, wherein performing post-epitaxial growth processing includes adding to the selected portions at least one of electrodes, insulators, and metal components defining the laser devices.

24. The method according to claim 22, further comprising the step of disposing an external mirror in proximity to the epitaxial layers before optically pumping the selected portions.

25. A method of manufacturing semiconductor laser devices on a wafer, comprising:

growing epitaxial layers on the wafer, the epitaxial layers forming at least one mirror and an active gain region;

optically pumping selected regions of the active gain region with a pump light source;

analyzing laser light emitted from each of the selected regions in response to the optical pumping; and identifying the wafer for sorting based on the analysis of the emitted light.

26. The method according to claim 25, where the regions corresponding to the semiconductor laser devices are sequentially optically pumped along successive rows and columns of the regions.

27. The method according to claim 25, further comprising the steps of:

performing post epitaxial growth processing on the wafer if the wafer is identified as having a selected characteristic.

28. The method according to claim 27, wherein the step of performing post epitaxial growth processing on the wafer includes forming an electrical contact on the wafer.

29. The method according to claim 25, further comprising the step of discarding the wafer when the wafer is identified for sorting as failing to meet a selected criterion.

30. The method according to claim 25, further comprising the step of disposing a mirror in proximity to the wafer before optical pumping.

31. The method according to claim 25, wherein the mirror disposed in proximity to the wafer before optical pumping is external to the active gain region.

* * * * *